United States Patent
Park et al.

(10) Patent No.: US 10,490,409 B2
(45) Date of Patent: Nov. 26, 2019

(54) PRECURSOR FOR VAPOR DEPOSITION HAVING EXCELLENT THERMAL STABILITY AND PREPARING METHOD THEREOF

(71) Applicant: HANSOL CHEMICAL CO., LTD, Seoul (KR)

(72) Inventors: Jung-Woo Park, Seoul (KR); Hong-Ki Kim, Seoul (KR); Mi-Ra Park, Jeollabuk-do (KR); Jun-Hyuck Kwon, Chungcheongbuk-do (KR)

(73) Assignee: Hansol Chemical Co., Ltd., Seoul (KR)

( * ) Notice: Subject to any disclaimer, the term of this patent is extended or adjusted under 35 U.S.C. 154(b) by 82 days.

(21) Appl. No.: 15/659,163

(22) Filed: Jul. 25, 2017

(65) Prior Publication Data

US 2018/0122645 A1    May 3, 2018

(30) Foreign Application Priority Data

Oct. 28, 2016 (KR) .................. 10-2016-0141582
Mar. 14, 2017 (KR) .................. 10-2017-0031848

(51) Int. Cl.
*H01L 21/28* (2006.01)
*C23C 16/455* (2006.01)
(Continued)

(52) U.S. Cl.
CPC ........ *H01L 21/28194* (2013.01); *C07F 17/00* (2013.01); *C23C 16/405* (2013.01); *C23C 16/45525* (2013.01); *H01L 21/0228* (2013.01); *H01L 21/02181* (2013.01); *H01L 21/02186* (2013.01); *H01L 21/02189* (2013.01); *H01L 21/02205* (2013.01); *H01L 29/517* (2013.01)

(58) Field of Classification Search
CPC ............. H01L 21/28194; H01L 29/517; H01L 21/02189; H01L 21/02181; H01L 21/0228; H01L 21/02205; H01L 21/02186; C07F 17/00; C23C 16/405; C23C 16/45525

See application file for complete search history.

(56) References Cited

U.S. PATENT DOCUMENTS

2013/0337659 A1* 12/2013 Ahn .................. C23C 16/18
                                                         438/785

FOREIGN PATENT DOCUMENTS

KR    10-2012-0105070 A    9/2012
KR    10-2013-0091450 A    8/2013
KR    10-2014-0078534 A    6/2014

OTHER PUBLICATIONS

R. Katamreddy et al., Advanced Precursor Development for Sr and Ti Based Oxide Thin Film Applications, ECS Transactions, 2009, vol. 25, No. 4, pp. 217-230.

(Continued)

*Primary Examiner* — William F Kraig
*Assistant Examiner* — Vicki B. Booker
(74) *Attorney, Agent, or Firm* — Baker & Hostetler LLP

(57) ABSTRACT

The present invention relates to a vapor deposition compound which serves to deposit a thin film through vapor deposition. More particularly, the present invention relates to vapor deposition zirconium, titanium, and hafnium precursors which are applicable to atomic layer deposition (ALD) or chemical vapor deposition (CVD) and which have low viscosity, excellent thermal stability, and fast self-saturation, and a method of preparing the same.

6 Claims, 13 Drawing Sheets

(51) Int. Cl.
    *H01L 21/02*     (2006.01)
    *C07F 17/00*     (2006.01)
    *C23C 16/40*     (2006.01)
    *H01L 29/51*     (2006.01)

(56) References Cited

OTHER PUBLICATIONS

R. Pheamhom et al., "Characteristics of atomic layer deposited TiO2 films and their photocatalytic activity," Journal of Vacuum Science & Technology A: Vacuum, Surfaces, and Films, vol. 24, No. 4, 2006, pp. 1535-1539.

Dennis M. Hausmann et al., "Atomic Layer Deposition of Hafnium and Zirconium Oxides Using Metal Amide Precursors," Chem. Materials, vol. 14, 2002, pp. 4350-4358.

Kigsley Andrew James; "Studies in Early Transistion Metal Organometallic Chemistry"; Durham University; 1998; 300 pages.

\* cited by examiner

| EXAMPLE 1 | |
|---|---|
| PROCESSING TEMPERATURE | 320 °C |
| Uniformity | 4.92 % |

| COMPARATIVE EXAMPLE 2 | |
|---|---|
| PROCESSING TEMPERATURE | 320 °C |
| Uniformity | 15.23 % |

PRECURSOR FOR VAPOR DEPOSITION HAVING EXCELLENT THERMAL STABILITY AND PREPARING METHOD THEREOF

BACKGROUND OF THE INVENTION

1. Technical Field

The present invention relates to a vapor deposition compound which serves to deposit a thin film through vapor deposition. More particularly, the present invention relates to vapor deposition zirconium, titanium, and hafnium precursors which are applicable to atomic layer deposition (ALD) or chemical vapor deposition (CVD) and which have low viscosity, excellent thermal stability, and fast self-saturation, and a method of preparing the same.

2. Description of the Related Art

A gate oxide film (=a gate dielectric) used in the gate structure of a MOSFET (metal-oxide-semiconductor field effect transistor), which is the core of current electronic devices, is based on silicon oxide. $SiO_2$ has been most widely used as a gate dielectric due to low leakage current and excellent interfacial characteristics with Si substrates, thermodynamic stability, compatibility with conventional processes, and reliability. Currently, however, problems such as an increase in leakage current and the formation of a gate depletion layer are occurring due to a thin oxide film resulting from the size reduction and high integration of devices. In the case of $SiO_2$, as the size of the device is reduced, an operating voltage is lowered and a drive current is reduced. Therefore, in order to improve the performance of the device, a drive current amount and a gate capacitance must be increased together. However, in a MOS (metal-oxide-semiconductor) of 0.1 μm or less, $SiO_2$ has a physical limitation as a gate dielectric. As the thickness of $SiO_2$ is decreased, the amount of a leakage current is greatly increased due to direct tunneling, thus limiting application to low-power-consumption devices. In the case of a conventional device using $SiO_2$ as a gate dielectric, there is a limit on the use thereof as a low power device, and a large hating value attributable to leakage current is considered to be a problem even in a high-performance device. In order to solve the problems, many attempts have been made to use new oxides having high dielectric permitivity.

Therefore, as the conditions of the gate dielectric to replace $SiO_2$, high dielectric constant, thermodynamic stability, high temperature stability, thin film uniformity, interfacial characteristics with silicon substrates, compatibility with MOS process technology, and reliability are required. Oxide films ($ZrO_2$, $TiO_2$, $HfO_2$, etc.) containing Zr, Ti, or Hf are considered to be materials that satisfy the above-described requirements. Atomic layer deposition (ALD) and chemical vapor deposition (CVD) are the most suitable deposition techniques for forming the thin film and controlling the physical properties. Atomic layer deposition is expected to solve problems, such as high leakage current, caused by a size reduction of devices, and may be readily applicable to the deposition of thin films with an atomic-level composition change and to nanoscale devices. Further, chemical vapor deposition is a technique for performing uniform deposition on a substrate which has a complicated shape and excellent adhesion. Chemical vapor deposition is available for the deposition of substances with high purity, thus being widely used in various applications such as abrasion-resistant or corrosion-resistant coating.

Meanwhile, Korean Laid-Open Patent Application Nos. 10-2012-0105070 and 10-2014-0078534 have been filed as applications related to zirconium compounds and $ZrO_2$ thin films, but the structure of the compound is different from that of the present application, and there are limits in the reduction of viscosity and in the extent to which the uniformity of thin film deposition can be improved.

SUMMARY OF THE INVENTION

Accordingly, the present invention is intended to provide novel vapor deposition zirconium, titanium, and hafnium compounds which are applicable to atomic layer deposition (ALD) or chemical vapor deposition (CVD).

Particularly, it is an object of the present invention to provide zirconium, titanium, and hafnium compounds which have excellent thermal stability, do not cause side reactions resulting from processing residues, and have low viscosity, thus being useful for vapor deposition, a precursor including the same, and a method of preparing the same.

However, the problems to be solved by the present application are not limited to the above-mentioned problems, and other matters that are not mentioned can be clearly understood by those skilled in the art from the following description.

An aspect of the present application provides the compound represented by the following Chemical Formula 1.

[Chemical Formula 1]

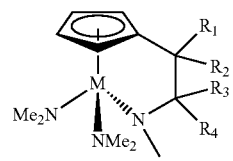

In Chemical Formula 1,

M is any one selected from among Zr, Ti, and Hf, $R_1$ to $R_4$ are each independently hydrogen, a substituted or unsubstituted linear or branched saturated or unsaturated alkyl group having 1 to 3 carbon atoms, or an isomer thereof, and Me is a methyl group.

Another aspect of the present application provides a vapor deposition precursor including the compound.

Still another aspect of the present application provides a thin film in which the vapor deposition precursor is deposited.

Yet another aspect of the present application provides a method of preparing a thin film, the method including introducing the vapor deposition precursor into a chamber.

Still yet another aspect of the present application provides a multilayered thin film including one or more of the thin films.

A further aspect of the present application provides a memory device including one or more of the thin films.

Novel vapor deposition zirconium, titanium, and hafnium compounds according to the present invention and a precursor including the vapor deposition compound have excellent thermal stability, thus enabling thin film deposition at high temperatures. Further, the amount of residue attributable to heat loss is small, thus preventing side reactions of a process.

Further, since the vapor deposition precursor of the present invention has a low viscosity, uniform thin film deposition is possible. Accordingly, excellent physical properties of the thin film, fast self-saturation, and thickness and step-covering ability can be ensured.

Such physical properties provide a precursor suitable for atomic layer deposition and chemical vapor deposition, and application to a gate dielectric material can be expected through the manufacture of a thin film in which the precursor is deposited.

DESCRIPTION OF THE SPECIFIC EMBODIMENTS

Figure 1:
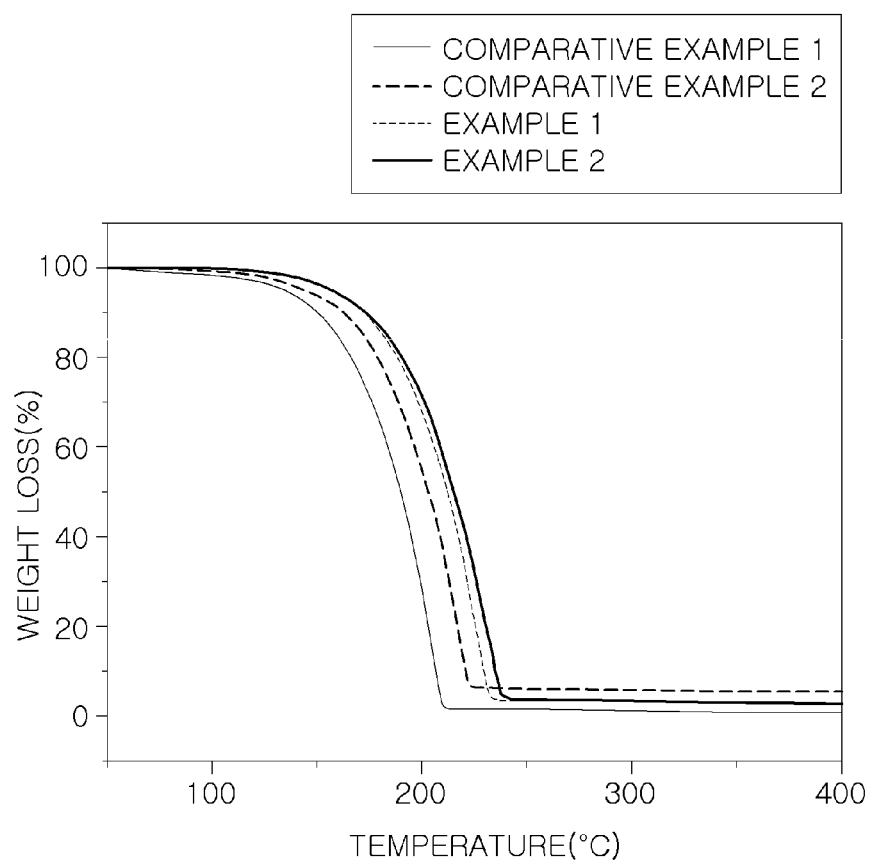
FIG. 1 is a comparative thermogravimetric analysis (TGA) graph showing the thermal decomposition characteristics of zirconium precursors according to Examples and Comparative Examples.

The present invention will be described more fully hereinafter with reference to the accompanying drawings, in which embodiments and examples of the present application are shown so as to enable easy understanding by a person with ordinary skill in the art. The present application may, however, be embodied in many different forms, and should not be construed as being limited to the embodiments and examples set forth herein. In order to clearly illustrate the present invention, parts not related to the description are omitted from the drawings.

Throughout the specification of the present application, when a member is located "on" another member, it includes not only the case where a member is in contact with another member but also the case where another member exists between the two members.

Throughout the specification of the present application, when any portion "includes" any component, this means that the portion does not exclude other components but may further include other components unless otherwise stated.

Also, throughout the specification of the present specification, the phrase "step" or "step of" does not mean "step for".

Hereinafter, embodiments and examples of the present application will be described in detail with reference to the accompanying drawings. However, the present application is not limited to these embodiments and examples and drawings.

An aspect of the present application provides the compound represented by the following Chemical Formula 1.

[Chemical Formula 1]

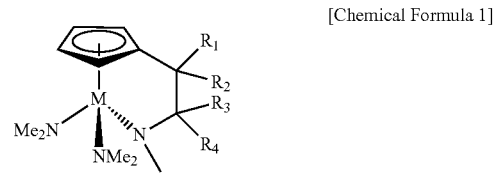

In Chemical Formula 1,

M is any one selected from among Zr, Ti, and Hf, $R_1$ to $R_4$ are each independently hydrogen, a substituted or unsubstituted linear or branched saturated or unsaturated alkyl group having 1 to 3 carbon atoms, or an isomer thereof, and Me is a methyl group.

In an embodiment of the present application, the compound represented by Chemical Formula 1 may be preferably represented by any one of the following Chemical Formulas.

[Chemical Formula 1-1]

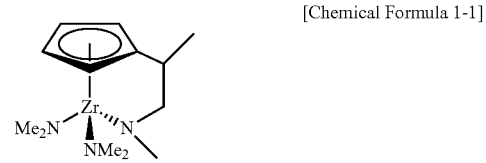

[Chemical Formula 1-2]

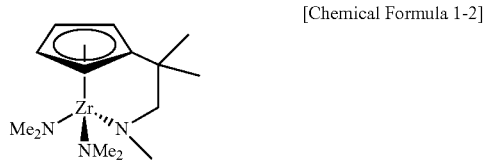

[Chemical Formula 1-3]

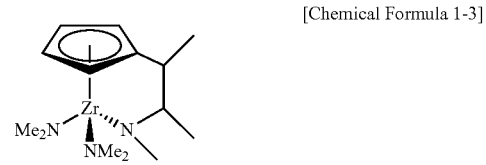

-continued

[Chemical Formula 1-4]

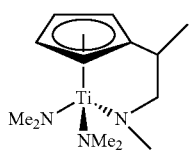

[Chemical Formula 1-5]

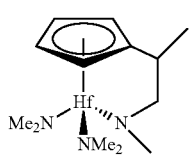

In the embodiment of the present application, the compound of Chemical Formula 1 may be liquid or volatile at room temperature. In atomic layer deposition (ALD), reactants must be highly volatile, stable, and highly reactive. In atomic layer deposition (ALD), reaction raw materials are supplied separately, and thin films including one or less layer grow due to a surface reaction during one cycle of deposition. Ligands of the reaction raw materials adsorbed on the substrate are chemically reacted with other reaction raw materials that are subsequently supplied, thereby being removed. When the precursor compound, which is a reactant, is heated for the atomic layer deposition, it may be preferable for the precursor compound to be in a liquid phase than in a solid phase in view of reaction speed and processing.

Another aspect of the present application provides a vapor deposition precursor including the compound.

In the embodiment of the present application, the vapor deposition may include atomic layer deposition (ALD) or chemical vapor deposition (CVD), and the chemical vapor deposition may include metal organic chemical vapor deposition (MOCVD).

In the embodiment of the present application, the vapor deposition precursor may be dissolved in one or more organic solvents selected from among hexane, octane, and cyclopentyl methyl ether (CPME), without being limited thereto. Preferably, the vapor deposition precursor may be dissolved in one or more organic solvents selected from among octane and cyclopentyl methyl ether, without being limited thereto.

Still another aspect of the present application provides a thin film in which the vapor deposition precursor is deposited.

Yet another aspect of the present application provides a method of preparing a thin film, the method including introducing the vapor deposition precursor into a chamber. The introducing the vapor deposition precursor into the chamber may include physical adsorption, chemical adsorption, or physical and chemical adsorption.

In the embodiment of the present application, the method may further include dissolving the vapor deposition precursor in one or more organic solvents, selected from among hexane, octane, and cyclopentyl methyl ether, in order to supply the vapor deposition precursor. In the vapor deposition, the precursor, that is, a source gas, may be supplied so as to reduce viscosity via a liquid delivery system using an organic solvent as a diluent for movement to a deposition chamber into which the substrate is introduced and for efficiency of spraying. Commonly used hexanes are not human-friendly and contain regulated materials, which makes application to actual processes difficult. Further, loss occurs during the dilution process due to the high boiling point thereof. Accordingly, the present invention proposes octane or cyclopentyl methyl ether, which is a non-regulated material, as a diluent.

In the embodiment of the present application, the method of preparing the thin film may include atomic layer deposition (ALD) or chemical vapor deposition (CVD), and the chemical vapor deposition may include metal organic chemical vapor deposition (MOCVD).

Still yet another aspect of the present application provides a multilayered thin film including one or more of the thin films.

A further aspect of the present application provides a memory device including one or more of the thin films.

Hereinafter, the present application will be described in more detail using Examples, but the present application is not limited thereto.

All of the reagents used in the present Examples are those which are generally commercially available, and they are used without special purification unless specifically described.

EXAMPLE 1

Preparation of $CpCH(CH_3)CH_2NMeZr(NMe_2)_2$ 124.70 g (0.47 mol) of tetrakis-dimethylamino zirconium was quantitatively charged in a 500 mL flask, was diluted by adding 200 mL of hexane, and was agitated at 0° C., and 73.38 g (0.53 mol) of N-methyl 2-cyclopenbadienyl propylamine was slowly added thereto. Agitation was performed for about 16 hours, thus finishing the reaction and removing a solvent and volatile byproducts in a vacuum. The orange liquid that remained was subjected to vacuum distillation, thus obtaining 92.7 g (yield: 57%) of $CpCH(CH_3)CH_2NMeZr(NMe_2)_2$ of [Chemical Formula 1-1], which was a pale yellow liquid compound.

Boiling point (b.p): 105~110° C. @ 0.2 torr.

$^1$HNMR ($C_6D_6$) :δ 1.24 ($C_5H_4CH(C\underline{H}_3)CH_2N(CH_3)$, d, 3H),

δ 2.93 ($[(C\underline{H}_3)_2N]$-Zr, s, 6H),
δ 2.95 ($[(C\underline{H}_3)_2N]$-Zr, s, 6H),
δ 3.06 ($C_5H_4CH(CH_3)CH_2N(C\underline{H}_3)$, s, 3H),
δ 3.11 ($C_5H_4C\underline{H}(CH_3)CH_2N(CH_3)$, q, 1H),
δ 3.64 ($C_5H_4CH(CH_3)C\underline{H}_2N(CH_3)$, m, 2H),
δ 5.76 ($C_5\underline{H}_4CH(CH_3)CH_2N(CH_3)$, m, 1H),
δ 5.88 ($C_5\underline{H}_4CH(CH_3)CH_2N(CH_3)$, m, 1H),
δ 6.02 ($C_5\underline{H}_4CH(CH_3)CH_2N(CH_3)$, m, 1H),
δ 6.06 ($C_5\underline{H}_4CH(CH_3)CH_2N(CH_3)$, m, 1H)

EXAMPLE 2

Preparation of $CpC(CH_3)_2CH_2NMeZr(NMe_2)_2$ 9.55 g (0.04 mol) of tetrakis-dimethylamino zirconium was quantitatively charged in a 250 mL flask, was diluted by adding 60 mL of hexane, and was agitated at 0° C., and 12.27 g (0.04 mol) of 2-(cyclopentadienyl)-N,2-dimethylpropanamine was slowly added thereto. Agitation was performed for about 16 hours, thus finishing the reaction and removing a solvent and volatile byproducts in a vacuum. The orange liquid that remained was subjected to vacuum distillation, thus obtaining 8.21 g (yield: 70%) of $CpC(CH_3)_2CH_2NMeZr(NMe_2)_2$ of [Chemical Formula 1-2], which was a pale yellow liquid compound.

Boiling point (b.p): 120° C. @ 0.2 torr.

$^1$HNMR ($C_6D_6$) :δ 1.35 ($C_5H_4CH(C\underline{H}_3)_2CH_2N(CH_3)$, s, 6H),

δ 2.94 ([(C$\underline{H}_3$)$_2$N]-Zr, s, 12H),
δ 3.03 (C$_5$$\underline{H}_4$CH(CH$_3$)$_2$CH$_2$N(C$\underline{H}_3$), s, 3H),
δ 3.55 (C$_5$H$_4$CH(CH$_3$)$_2$C$\underline{H}_2$N(CH$_3$), s, 2H),
δ 5.82 (C$_5$$\underline{H}_4$CH(CH$_3$)$_2$CH$_2$N(CH$_3$), t, 2H),
δ 6.07 (C$_5$$\underline{H}_4$CH(CH$_3$)$_2$CH$_2$N(CH$_3$), t, 2H)

EXAMPLE 3

Preparation of CpC(CH$_3$)$_2$CH$_2$NMeTi(NMe$_2$)$_2$ 680.77 g (3.04 mol) of tetrakis-dimethylamino titanium was quantitatively charged in a 5 L Schlenk flask, was diluted by adding 783 mL of toluene, and was agitated at 0° C., and 500.00 g (3.64 mol) of N-methyl 2-cyclopentadienyl propylamine, which was diluted in 575 mL of toluene, was slowly added thereto. Agitation was performed for about 16 hours, thus finishing the reaction and removing a solvent and volatile byproducts in a vacuum. The dark brown liquid that remained was subjected to vacuum distillation, thus obtaining 620.18 g (yield: 76%) of CpCH(CH$_3$)CH$_2$NMeTi(NMe$_2$)$_2$ of [Chemical Formula 1-4], which was an orange liquid compound.
Boiling point (b.p): 98° C. @ 0.2 torr.
$^1$HNMR (C$_6$D$_6$):δ 1.22 (C$_5$H$_4$CH(C$\underline{H}_3$)CH$_2$N(CH$_3$), d, 3H),
δ 3.06 ([(C$\underline{H}_3$)$_2$N]-Ti, s, 6H),
δ 3.11 ([(C$\underline{H}_3$)$_2$N]-Ti, s, 6H),
δ 3.32 (C$_5$$\underline{H}_4$CH(CH$_3$)CH$_2$N(C$\underline{H}_3$), s, 3H),
δ 3.06 (C$_5$H$_4$C$\underline{H}$(CH$_3$)CH$_2$N(CH$_3$), q, 1H),
δ 3.62 (C$_5$H$_4$CH(CH$_3$)C$\underline{H}_2$N(CH$_3$), m, 2H),
δ 5.69 (C$_5$$\underline{H}_4$CH(CH$_3$)CH$_2$N(CH$_3$), m, 1H),
δ 5.76 (C$_5$$\underline{H}_4$CH(CH$_3$)CH$_2$N(CH$_3$), m, 1H),
δ 5.86 (C$_5$$\underline{H}_4$CH(CH$_3$)CH$_2$N(CH$_3$), m, 1H),
δ 5.90 (C$_5$$\underline{H}_4$CH(CH$_3$)CH$_2$N(CH$_3$), m, 1H)

EXAMPLE 4

Preparation of CpC(CH$_3$)$_2$CH$_2$NMeHf(NMe$_2$)$_2$ 124.89 g (0.352 mol) of tetrakis-dimethylamino hafnium was quantitatively charged in a 500 mL flask, was diluted by adding 220 mL of toluene, and was agitated at 0° C., and 49.68 g (0.352 mol) of N-methyl 2-cyclopentadienyl propylamine, diluted in 60 mL of n-hexane, was slowly added thereto. Agitation was performed for about 16 hours, thus finishing the reaction and removing a solvent and volatile byproducts in a vacuum. The yellow liquid that remained was subjected to vacuum distillation, thus obtaining 128.42 g (yield: 93%) of CpCH(CH$_3$)CH$_2$NMeHf(NMe$_2$)$_2$ of [Chemical Formula 1-5], which was a colorless liquid compound.
Boiling point (b.p): 110° C. @ 0.2 torr.
$^1$HNMR (C$_6$D$_6$):δ 1.22 (C$_5$H$_4$CH(C$\underline{H}_3$)CH$_2$N(CH$_3$), d, 3H),
δ 2.98 ([(C$\underline{H}_3$)$_2$N]-Hf, s, 6H),
δ 3.00 ([(C$\underline{H}_3$)$_2$N]-Hf, s, 6H),
δ 3.06 (C$_5$$\underline{H}_4$CH(CH$_3$)CH$_2$H(C$\underline{H}_3$), s, 3H),
δ 3.10 (C$_5$H$_4$C$\underline{H}$(CH$_3$)CH$_2$N(CH$_3$), q, 1H),
δ 3.74 (C$_5$H$_4$CH(CH$_3$)C$\underline{H}_2$N(CH$_3$), m, 2H),
δ 5.71 (C$_5$$\underline{H}_4$CH(CH$_3$)CH$_2$N(CH$_3$), m, 1H),
δ 5.86 (C$_5$$\underline{H}_4$CH(CH$_3$)CH$_2$N(CH$_3$), m, 1H),
δ 6.00 (C$_5$$\underline{H}_4$CH(CH$_3$)CH$_2$N(CH$_3$), m, 1H),
δ 6.03 (C$_5$$\underline{H}_4$CH(CH$_3$)CH$_2$N(CH$_3$), m, 1H)

PREPARATION EXAMPLE

Manufacture of Zirconium Oxide Thin Film

CpCH(CH$_3$)CH$_2$NMeZr(NMe$_2$)$_2$ prepared in Example 1 was deposited in a thin film using atomic layer deposition (ALD) equipment. The substrate used in the present experiment was a bare Si wafer and was cleaned by ultrasonication for 10 minutes in each of acetone, ethanol, and deionized water (DI water) prior to deposition. The bare Si wafer was dipped in a solution of 10% HF (HF:H$_2$O=1:9) for 10 seconds to remove a naturally occurring oxide thin film therefrom. The bare Si wafer, which was cleaned using HF, was immediately transferred to an atomic layer deposition (ALD) chamber. The temperature was maintained at 105° C. [The zirconium precursor of Example 1] (X seconds), [Ar] (10 seconds), [O$_3$] (Y seconds), and [Ar] (10 seconds) were sequentially supplied, supply in this manner was set as one cycle, and 100 cycles were carried out. The zirconium precursor of Example 1 was dissolved in one or more organic solvents (15 wt % or less) selected from among hexane, octane, and cyclopentyl methyl ether, and was supplied to the deposition chamber via a liquid delivery system. Although the selectivity of hexane, octane, and cyclopentyl methyl ether is not particularly limited in the present Preparation Example, the use of octane or cyclopentyl methyl ether is preferable. In the supply of the zirconium precursor in Example 1 (X seconds), which was a source gas, X was 3 to 15 seconds (3, 5, 7, 10, 13, and 15 seconds respectively), and the supply of ozone (O$_3$) (Y seconds), which was a reactive gas, was performed for 1 to 5 seconds (1, 3, and 5 seconds respectively). The flow rate of argon (Ar) was set to 100 sccm in order to perform purging, and ozone (O$_3$) which was the reactive gas was blown. Each reactive gas was injected by controlling the on/off of the pneumatic valve. The pressure of a reactor was set to 1 torr at a processing temperature (substrate temperature) ranging from 260° C. to 340° C.

EXPERIMENTAL EXAMPLE 1

Analysis of Characteristics of Vapor Deposition Zirconium Precursor

In analysis of the characteristics of the vapor deposition precursors prepared in Examples 1 to 4, Comparative Examples 1 and 2 shown in the following Table 1 were set as control groups, and thermogravimetric analysis (TGA), the temperature (T$_{1/2}$) at which the weight of the precursor was reduced by half, residues after thermal analysis, the viscosity, and a vaporization rate were each checked.

EXPERIMENTAL EXAMPLE 2

Analysis of Characteristics of Zirconium Oxide Thin Film

The uniformity of the zirconium precursors, which were prepared in Example 1 and Comparative Example 2, depending on deposition of the substrate was measured.
The following Table 1 shows the physical properties of the zirconium precursors which were prepared according to the present invention and which included CpCH(CH$_3$)CH$_2$NMeZr(NMe$_2$)$_2$ of Example 1, CpC(CH$_3$)$_2$CH$_2$NMeZr(NMe$_2$)$_2$ of Example 2, CpZr(NMe$_2$)$_3$ of Comparative Example 1, and CpCH$_2$CH$_2$NMeZr(NMe$_2$)$_2$ of Comparative Example 2.
The following Table 2 shows the physical properties of the precursors which were prepared according to the present invention and which included CpCH(CH$_3$)CH$_2$NMeZr(NMe$_2$)$_2$ of Example 1, CpCH(CH$_3$)CH$_2$NMeTi(NMe$_2$)$_2$ of Example 3, and CpCH(CH$_3$)CH$_2$NMeHf(NMe$_2$)$_2$ of Example 4.

TABLE 1

| | Example 1 | Example 2 | Comparative Example 1 | Comparative Example 2 |
|---|---|---|---|---|
| Chemical name 1 | $CpCH(CH_3)CH_2NMeZr(NMe_2)_2$ | $CpC(CH_3)_2CH_2NMeZr(NMe_2)_2$ | $CpZr(NMe_2)_3$ | $CpCH_2CH_2NMeZr(NMe_2)_2$ |
| Chemical name 2 | [2-(N-methylamino)1-methyl ethyl cyclopentadienyl] bis(dimethylamino) zirconium | [2-(N-methylamino)1,1'-dimethyl ethyl cyclopentadienyl] bis(dimethylamino) zirconium | Cyclopentadienyl tris(dimethyl amino)zirconium | [2-(N-methylamino) ethylcyclopentadienyl] bis(dimethylamino) zirconium |
| Structural formula | | | | |
| State (25° C.) | Pale yellow liquid | Pale yellow liquid | Pale yellow liquid | Pale yellow liquid |
| Molecular weight | 314.58 g/mol | 328.61 g/mol | 288.54 g/mol | 300.56 g/mol |
| Boiling point | 110° C. @ 0.3 torr | 120° C. @ 0.3 torr | 80° C. @ 0.1 torr | 95° C. @ 0.2 torr |

TABLE 2

| | Example 1 | Example 3 | Example 4 |
|---|---|---|---|
| Chemical name 1 | $CpCH(CH_3)CH_2NMeZr(NMe_2)_2$ | $CpCH(CH_3)CH_2NMeTi(NMe_2)_2$ | $CpCH(CH_3)CH_2NMeHf(NMe_2)_2$ |
| Chemical name 2 | [2-(N-methylamino)1-methyl ethyl cyclopentadienyl] bis(dimethylamino) zirconium | [2-(N-methylamino)1-methyl ethyl cyclopentadienyl] bis(dimethylamino) titanium | [2-(N-methylamino)1-methyl ethyl cyclopentadienyl] bis(dimethylamino) hafnium |
| Structural formula | | | |
| State (25° C.) | Pale yellow liquid | Orange liquid | Colorless liquid |
| Molecular weight | 314.58 g/mol | 217.22 g/mol | 401.85 g/mol |
| Boiling point | 110° C. @ 0.3 torr | 98° C. @ 0.2 torr | 110° C. @0 .2 torr |

Thermogravimetric analysis (TGA) was performed to measure the thermal stabilities of the precursors. The analysis was performed by heating the precursors to 400° C. at a rate of 10° C./min, and argon (Ar) gas was injected at a rate of 200 mL/min. The results of thermogravimetric analysis (TGA) of the zirconium precursors of Examples 1 and 2 and Comparative Examples 1 and 2 are shown in FIG. 1. It can be confirmed that the thermal stabilities of the zirconium precursors are higher in Examples 1 and 2 than in Comparative Examples 1 and 2.

Figure 2:
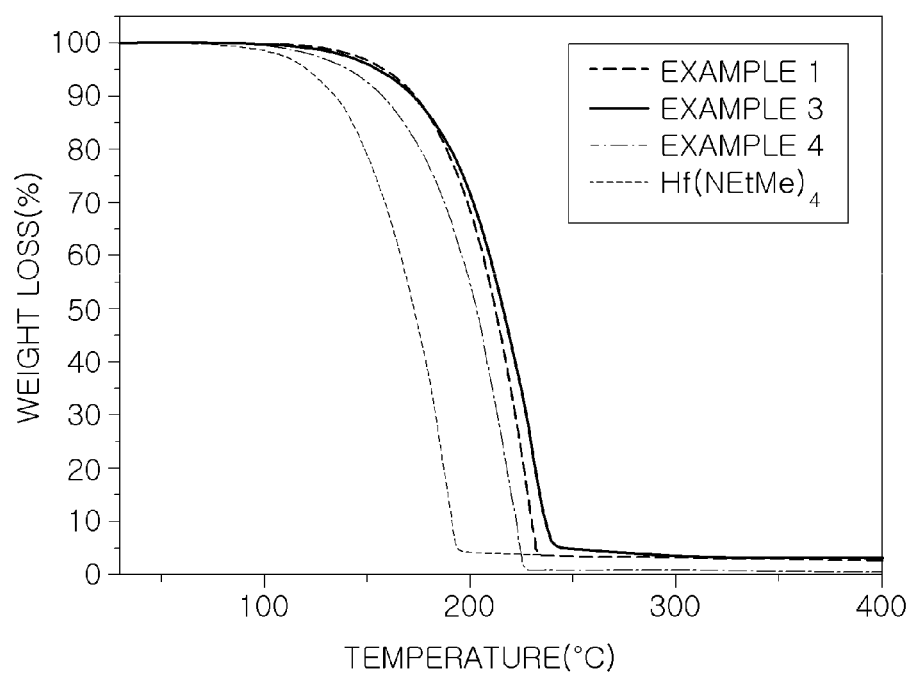
FIG. 2 is a comparative thermogravimetric analysis (TGA) graph showing the thermal decomposition characteristics of zirconium, titanium, and hafnium precursors according to the Examples.

FIG. 2 shows thermogravimetric analysis (TGA) of the precursors including zirconium, titanium, and hafnium as central metals according to Examples 1, 3 and 4, and of $Hf(NEtMe)_4$, which is a known precursor. The measurement procedure was the same as in FIG. 1. FIG. 2 is a comparative graph showing the thermogravimetric analysis of the precursors which include different center metals but have the same structure, and it was confirmed that all of the zirconium precursor of Example 1, the titanium precursor of Example 3, and the hafnium precursor of Example 4 showed very little change in weight even at around 150° C. and that heat resistance was ensured even at temperatures of 200° C. or higher. $CpTi(NMe_2)_3$ which is a conventional atomic layer deposition (ALD) precursor, is in a solid state at room temperature and has low thermal stability, thus exhibiting an ALD characteristic at 275° C. or lower (ECS Transactions, 2009, 25(4), 217). Also, $Ti(NMe_2)_4$, which is another precursor, has low thermal stability, thus exhibiting an ALD characteristic at 250° C. or lower (J. Vac. Sci. Technol. A, 2006, 24(4), 1535). In contrast thereto, the titanium precursor of Example 3 has thermal stability higher than that of the conventional precursors, thus being applicable to an atomic layer deposition (ALD) precursor at high temperatures.

Further, it has been reported that Hf(NEtMe)$_4$ exhibits an ALD characteristic up to 400° C. (Chem. Mater. 2002, 14, 4350). Accordingly, improved ALD characteristics may be expected from the hafnium precursor of Example 4, having thermal stability which is higher than that of Hf(NEtMe)$_4$.

Figure 3:
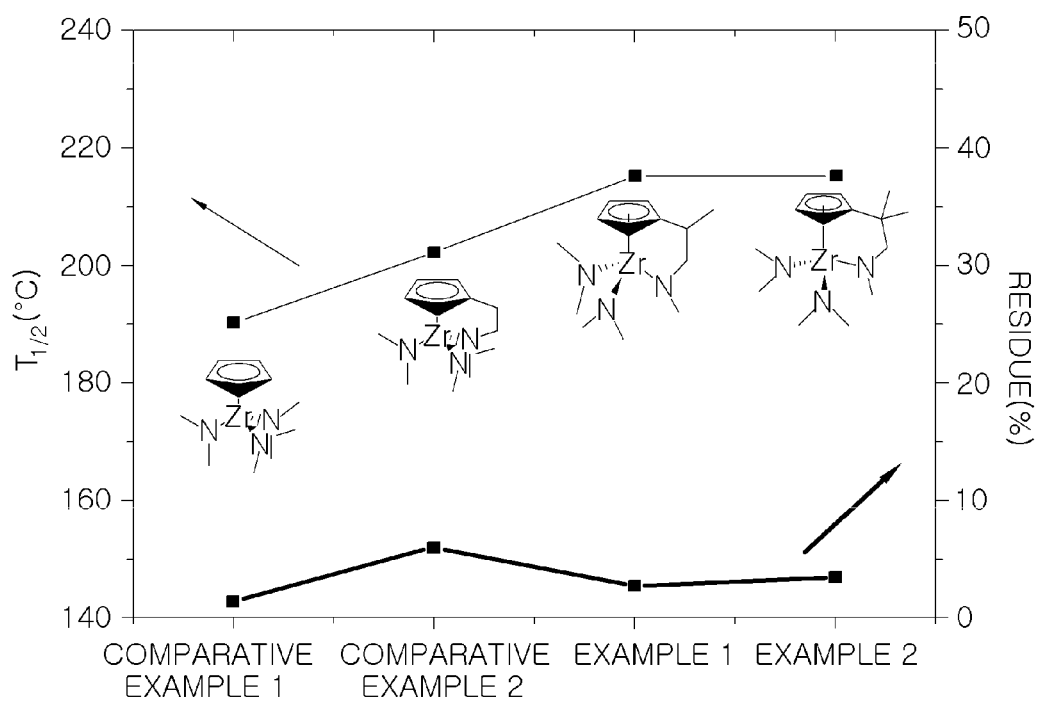
FIG. 3 is a graph showing a temperature ($T_{1/2}$) at which the weights of the zirconium precursors according to the Examples and the Comparative Examples are reduced by half, and solids remaining after thermogravimetric analysis (TGA)

FIG. 3 is a graph showing the temperature [$T_{1/2}$] at which the weights of the zirconium precursors are reduced by half. Compared to the Comparative Examples, in which a weight loss occurred at a temperature of less than about 210° C., the weights of the zirconium precursors of Examples 1 and 2 were reduced by half at a temperature of about 210° C. or higher, and accordingly, excellent thermal stability was confirmed, in addition to the results of FIG. 1. In the result of measurement of residue after the completion of thermogravimetric analysis, the amount of residue of the zirconium precursors of Examples 1 and 2 was smaller than that of Comparative Example 2, which was also effective in preventing side reactions from occurring during processing.

Figure 4:
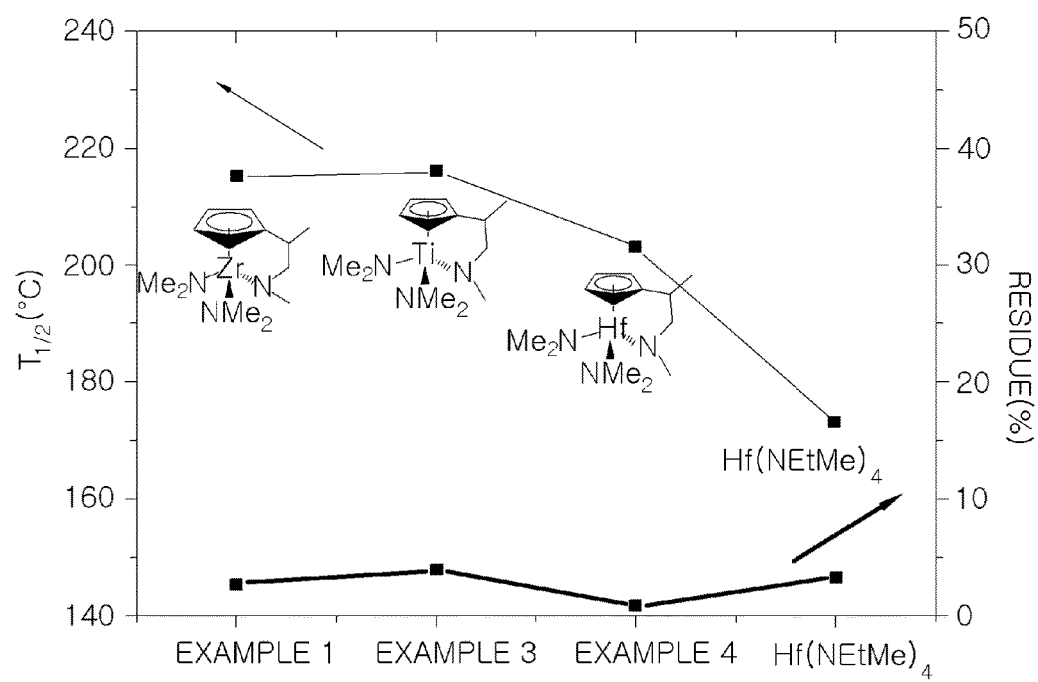
FIG. 4 is a graph showing the temperature ($T_{1/2}$) at which the weights of the zirconium, titanium, and hafnium precursors according to the Examples are reduced by half, and solids remaining after the thermogravimetric analysis (TGA)

FIG. 4 is a graph showing the temperature [$T_{1/2}$] at which the weights of the zirconium precursor of Example 1, the titanium precursor of Example 3, and the hafnium precursor of Example 4 are reduced by half, and residues. All of the temperatures at which the weights of the precursors were reduced by half were as high as about 200° C., and the content of the residues was found to be less than about 5%.

Figure 5:
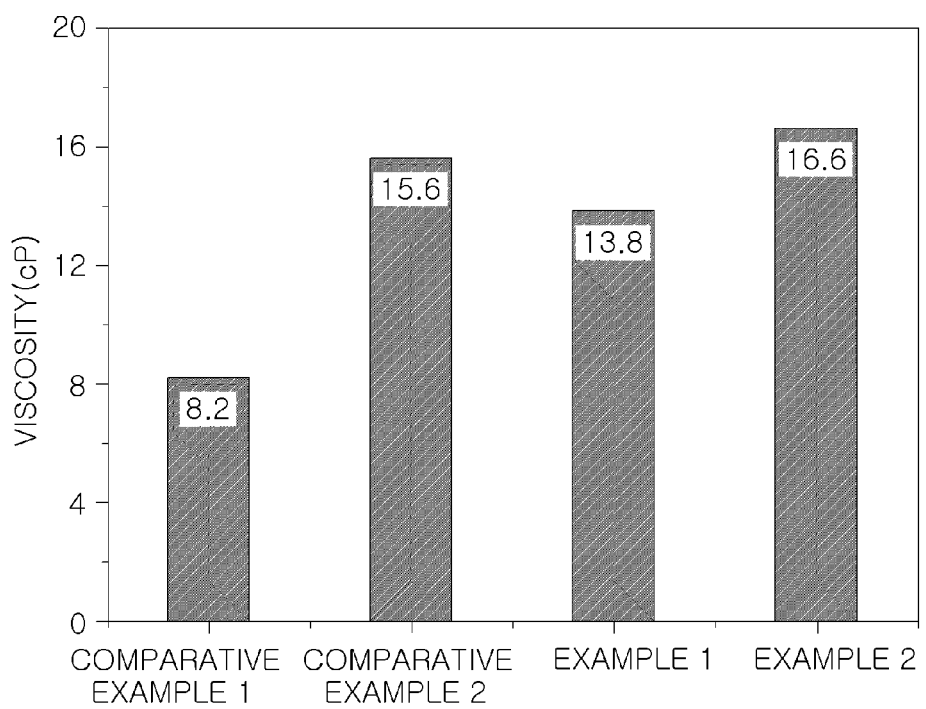
FIG. 5 is a graph showing the viscosities of the zirconium precursors according to the Examples and the Comparative Examples.

FIG. 5 is a graph obtained by measuring the viscosities of zirconium precursors. From the viscosity (13.8 cP) of the zirconium precursor of Example 1, it was confirmed that favorable properties were ensured during deposition of the thin film. The viscosity of the zirconium precursor of Example 1 was found to be lower than the viscosity (15.6 cP) of the zirconium precursor of Comparative Example 2.

Figure 6:
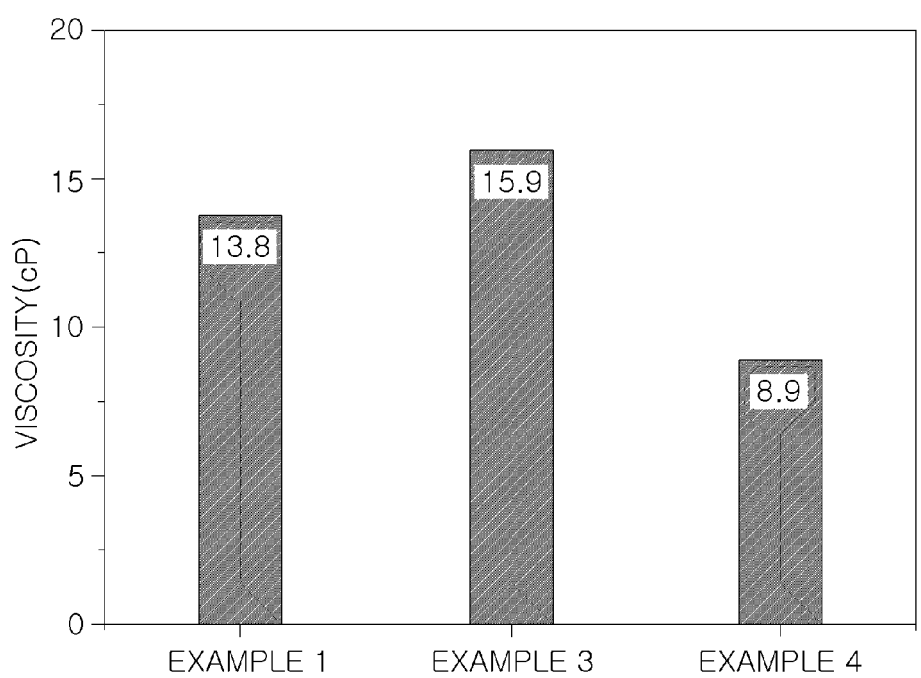
FIG. 6 is a graph showing the viscosities of the zirconium, titanium, and hafnium precursors according to the Examples.

FIG. 6 is a graph obtained by measuring the viscosities of the zirconium precursor of Example 1, the titanium precursor of Example 3, and the hafnium precursor of Example 4, and the measured values were obtained in the range of 8.9 to 15.9 cP.

Figure 7:
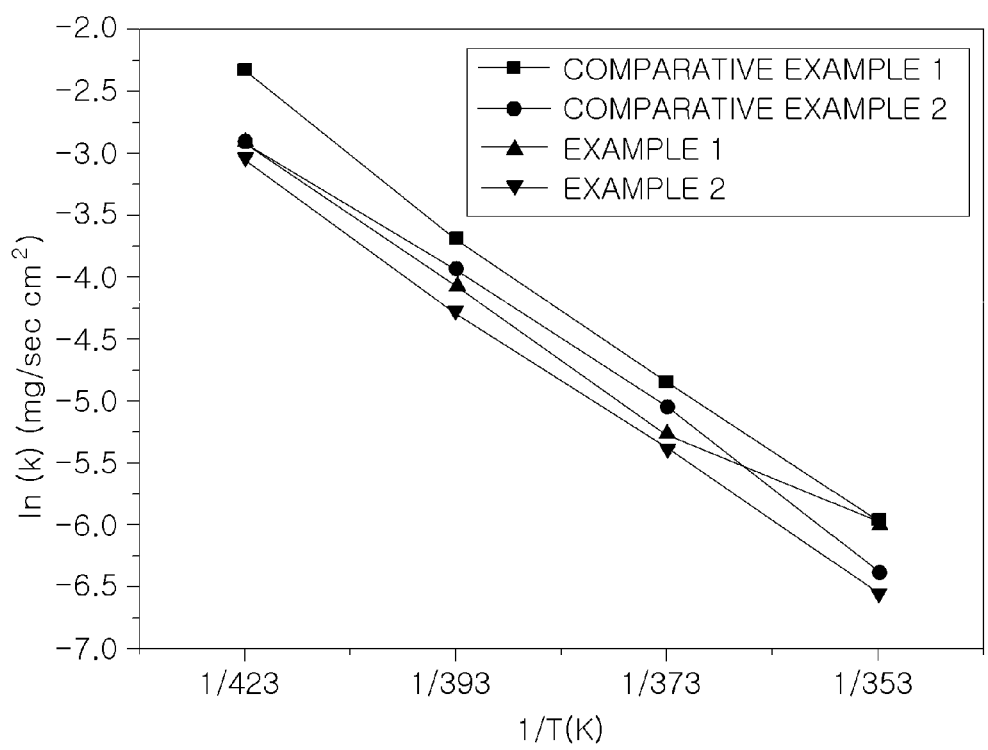
FIG. 7 is a graph showing the vaporization rates of zirconium precursors according to the Examples and the Comparative Examples.

The vaporization rate is measured as a rate constant K at a temperature of T and is expressed by ln(K), which is a linear function of 1/T. The experimental results of the vaporization rates during deposition of the thin films of the precursors of Examples 1 and 2 and Comparative Examples 1 and 2 are as shown in FIG. 7. From this drawing, it can be confirmed that the vaporization rates of the zirconium precursors prepared in Examples 1 and 2 are almost equal to those of the zirconium precursors prepared in Comparative Examples 1 and 2 (Example 1 (▲), Example 2 (▼), Comparative Example 1 (■), and Comparative Example 2 (●)).

Figure 8:
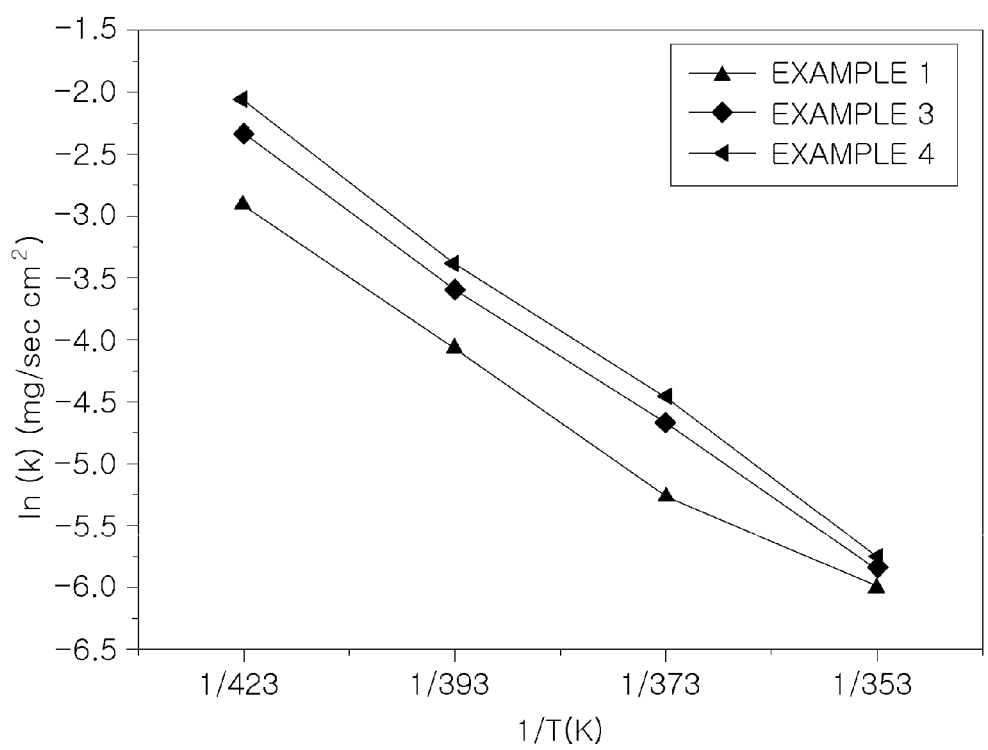
FIG. 8 is a graph showing the vaporization rates of zirconium, titanium, and hafnium precursors according to the Examples.

The experimental results of the vaporization rates during deposition of the thin films of the zirconium precursor of Example 1, the titanium precursor of Example 3, and the hafnium precursor of Example 4 are as shown in FIG. 8. Both the precursors prepared in Examples 3 and 4 exhibited an excellent vaporization rate compared to the precursor prepared in Example 1 (Example 1 (▲), Example 3 (♦), and Example 4 (□)).

Figure 9:
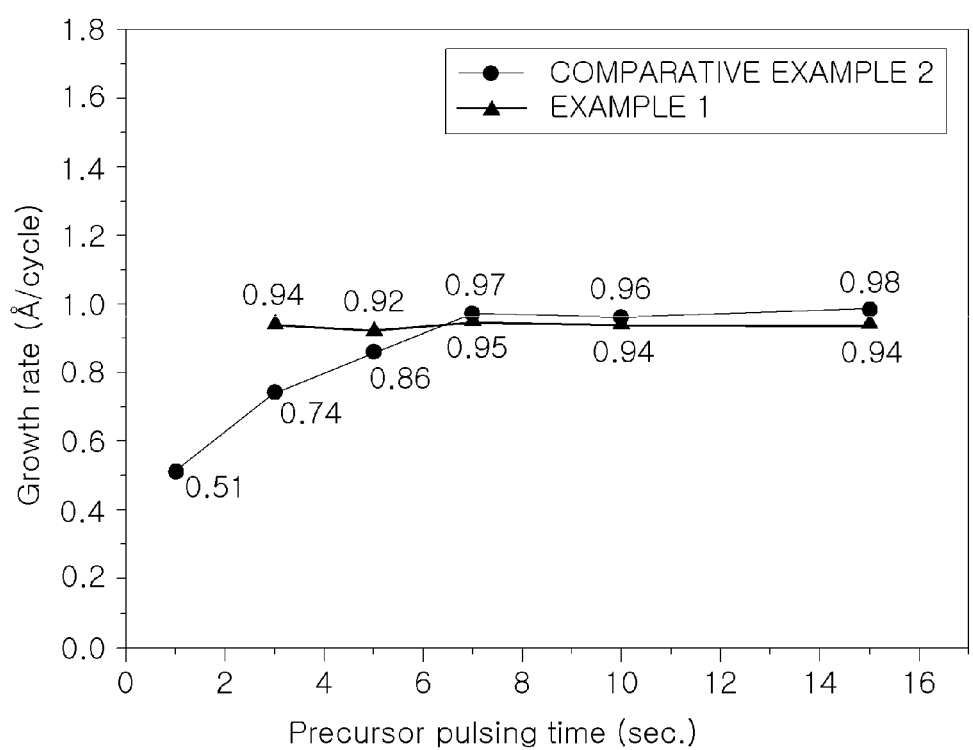
FIG. 9 is a graph showing the deposition rates of the thin films depending on the injection time of a source gas [precursor] during deposition of the thin films of the zirconium precursors according to the Example and the Comparative Example.

FIG. 9 is a graph showing the deposition rates of the thin films depending on the injection time of the zirconium precursor during deposition of the thin films. The sequential provision of [the zirconium precursor prepared in Example 1] (X seconds), [Ar] (10 seconds), [$O_3$] (Y seconds), and [Ar] (10 seconds) was set as one cycle, and 100 cycles were carried out to achieve deposition on the substrate. The zirconium precursor of Comparative Example 2 was deposited on the substrate using the same process. FIG. 9 shows the results obtained when injecting the zirconium precursor of Example 1, which is a source gas, for 3, 5, 7, 10, and 15 seconds, and when injecting the zirconium precursor of Comparative Example 2 for 1, 3, 5, 7, 10, and 15 seconds. The temperature of the substrate was set to 300° C., and the temperature of the zirconium precursor was set to 70° C. in Example 1 and 60° C. in Comparative Example 2. The other conditions were the same as those of the Preparation Examples.

Figure 10:
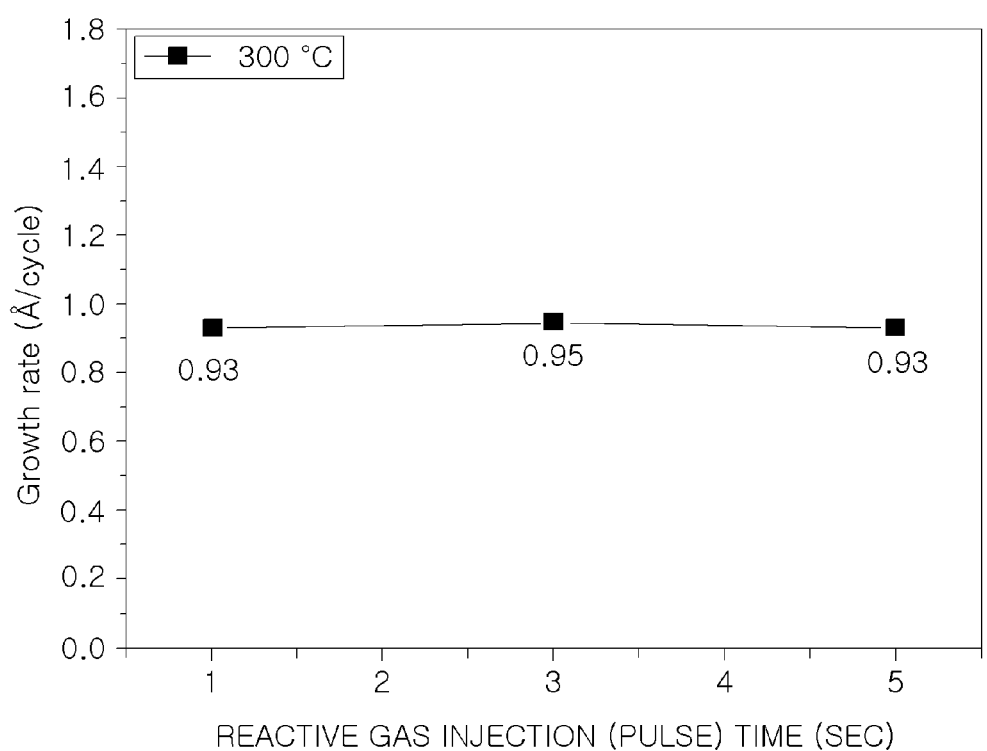
FIG. 10 is a graph showing the deposition rate of the thin film depending on the injection time of reactive gas during deposition of the thin film of the zirconium precursor prepared in Example 1.

FIG. 10 is a graph showing the deposition rate of the thin film of the zirconium precursor depending on the injection time of a reactive gas. The result was obtained by supplying ozone ($O_3$), which was the reactive gas, for 1, 3, and 5 seconds. The temperature of the substrate was set to 300° C., and the temperature of the zirconium precursor prepared in Example 1 was set to 70° C.

From FIG. 9, the result of deposition of the thin film depending on the injection time of the precursor can be confirmed. The zirconium precursor prepared in Comparative Example 2 starts to be self-saturated at 7 seconds, whereas the zirconium precursor prepared in Example 1 starts to be self-saturated at 3 seconds. Accordingly, since the zirconium precursor prepared in Example 1 is rapidly self-saturated during deposition of the thin films, it can be expected to improve the process yield.

The result of the deposition depending on the injection time of the reactive gas in FIG. 10 showed an excellent deposition rate of the thin film in the range of 0.93 to 0.95 Å/cycle when ozone ($O_3$) was injected for 1, 3 and 5 seconds. The temperature of the substrate was set to 300° C., and the temperature of the zirconium precursor of Example 1, which was the source gas, was set to 70° C. The other conditions were the same as those of the Preparation Examples.

Figure 11:
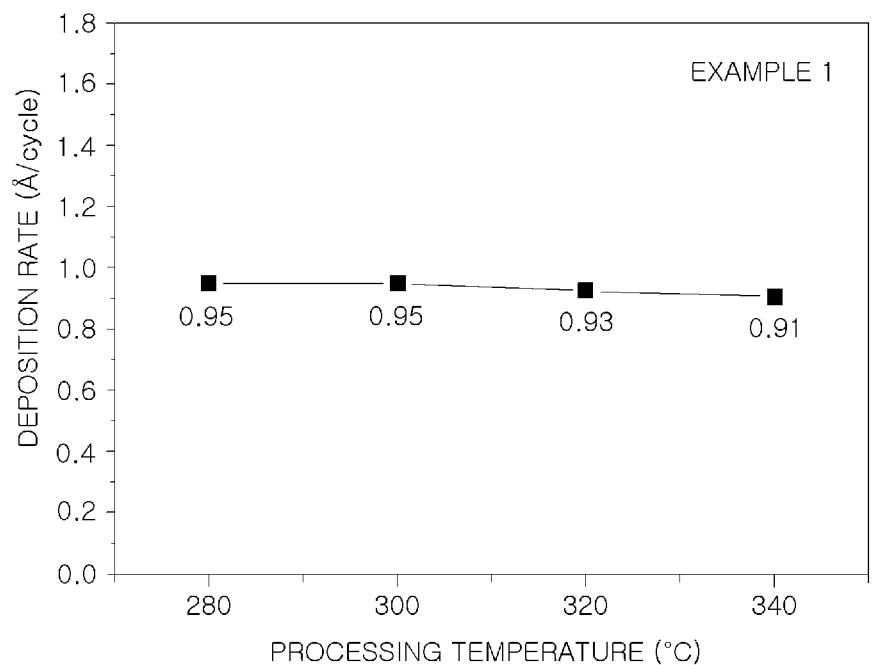
FIG. 11 is a graph showing the deposition rates of the thin films of the zirconium precursors according to the Example and the Comparative Example, depending on a processing temperature.
Figure 11:
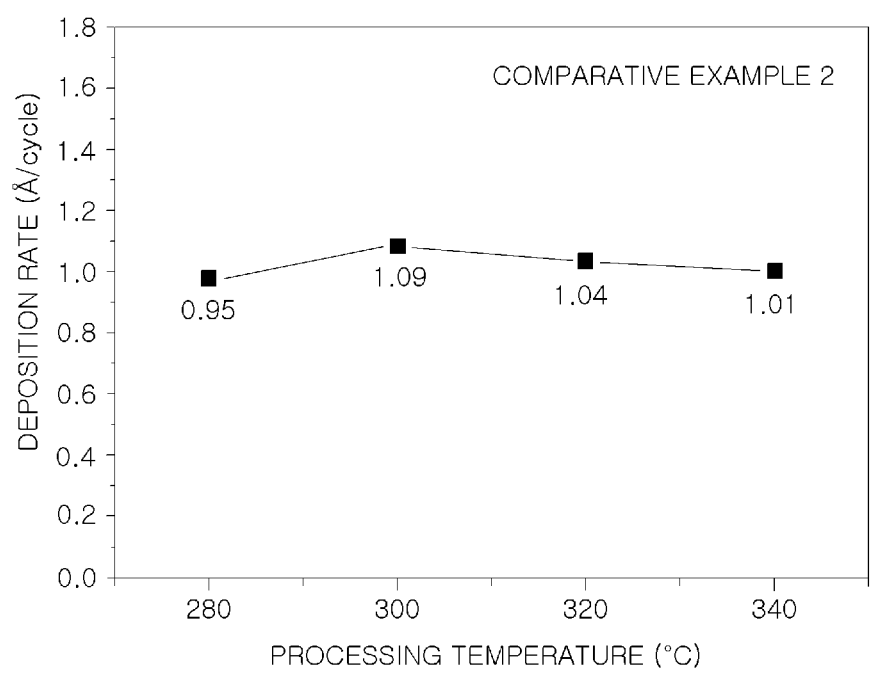

FIG. 11 is a graph showing the deposition rates of the thin films of the zirconium precursors according to Example 1 and Comparative Example 2 depending on processing temperature. "Processing temperature" in the present invention means the substrate temperature. The substrate temperature was set to 280 to 340° C. The deposition cycle of [the zirconium precursor of Example 1] (10 seconds), [Ar] (10 seconds), [$O_3$] (3 seconds), and [Ar] (10 seconds) was set as one cycle, and the flow rates of argon (Ar) were the same, and were set to 100 sccm. The zirconium precursor of Comparative Example 2 was deposited on the substrate using the same process. The deposition rate of the thin film of the zirconium precursor of Comparative Example 2 exhibited 0.98 to 1.09 Å/cycle at a substrate temperature of 280 to 340° C. However, since the difference in the deposition rate was relatively large depending on changes in temperature, it was difficult to perform film control. In contrast, the zirconium precursor of Example 1 exhibited a uniform deposition rate at 280° C. (0.95 Å/cycle), 300° C. (0.95 Å/cycle), 320° C. (0.93 Å/cycle), and 340° C. (0.91 Å/cycle) without a large difference in the deposition rate even when the temperature was changed, which was effective for film control.

Figure 12A:
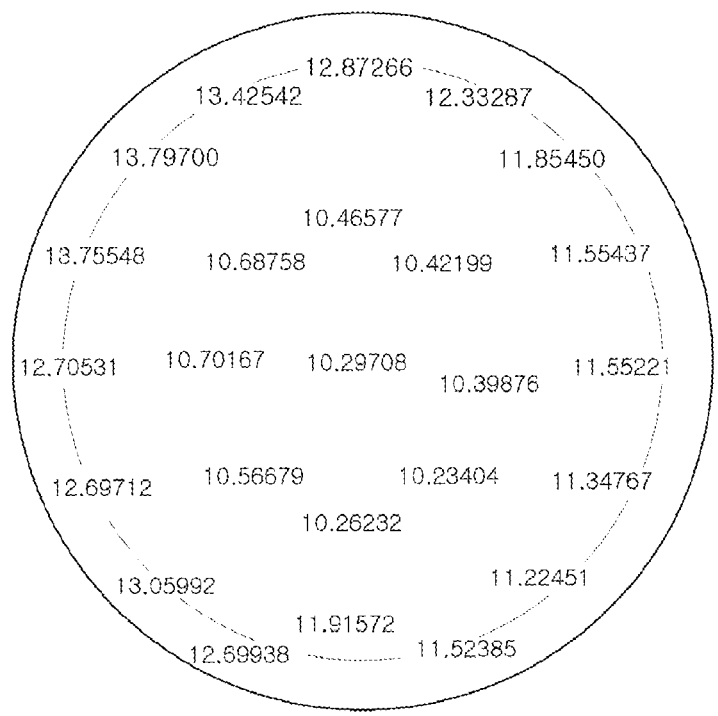
FIGS. 12A and 12B are an image showing the uniformities of the thin films deposited using the zirconium precursors of (a) Example 1 and (b) Comparative Example 2.
Figure 12B:
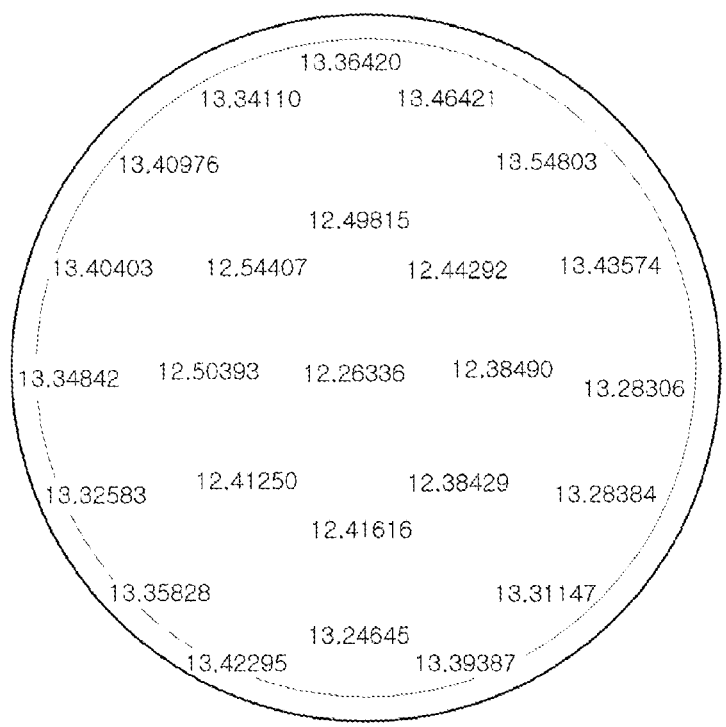

FIGS. 12A and 12B show the result of measurement of uniformity of the thin film obtained by depositing the zirconium precursor of Example 1 at a processing temperature of 320° C. The result of deposition of the thin film of Comparative Example 2 is also shown for comparison. The uniformity of the thin film obtained by depositing the zirconium precursor of Comparative Example 2 was 15.23%, and the uniformity of the thin film obtained by depositing the zirconium precursor of Example 1 was 4.92%. The lower the numerical value, the better the deposition uniformity of the thin film. When the uniformity value is high and non-uniformity is increased, the characteristics of the application device may deteriorate.

The scope of the present invention is defined by the appended claims rather than the detailed description, and it should be understood that all changes or modifications derived from the meaning and scope of the claims and equivalents thereof are included in the scope of the present invention.

What is claimed is:

1. A compound represented by any one of the following Chemical Formulas:

[Chemical Formula 1-1]

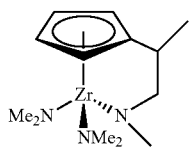

[Chemical Formula 1-2]

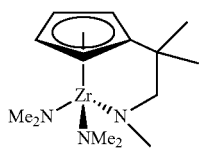

[Chemical Formula 1-3]

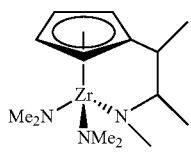

-continued

[Chemical Formula 1-4]

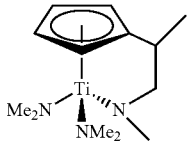

[Chemical Formula 1-5]

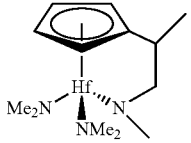

(Me is a methyl group).

2. A vapor deposition precursor comprising:
the compound of claim 1.

3. The vapor deposition precursor of claim 2, further comprising one or more organic solvents selected from among hexane, octane, and cyclopentyl methyl ether.

4. A method of preparing a thin film, the method comprising:
introducing the vapor deposition precursor of claim 2 on a substrate into a chamber.

5. The method of claim 4, further comprising:
dissolving the vapor deposition precursor in one or more organic solvents, selected from among hexane, octane, and cyclopentyl methyl ether, in order to supply the vapor deposition precursor.

6. The method of claim 4, wherein the method includes atomic layer deposition (ALD) or chemical vapor deposition (CVD).

* * * * *